US010143594B2

(12) United States Patent
Jackson

(10) Patent No.: US 10,143,594 B2
(45) Date of Patent: Dec. 4, 2018

(54) BANDAGE FOR REDUCING BLOOD LEAKAGE FROM AGGRESSIVE BLEEDING SITE

(71) Applicant: Derrick Jackson, Philadelphia, PA (US)

(72) Inventor: Derrick Jackson, Philadelphia, PA (US)

( * ) Notice: Subject to any disclaimer, the term of this patent is extended or adjusted under 35 U.S.C. 154(b) by 636 days.

(21) Appl. No.: 14/920,032

(22) Filed: Oct. 22, 2015

(65) Prior Publication Data
US 2016/0120705 A1 May 5, 2016

Related U.S. Application Data

(60) Provisional application No. 62/072,609, filed on Oct. 30, 2014.

(51) Int. Cl.
A61F 13/00 (2006.01)
A61F 5/30 (2006.01)

(52) U.S. Cl.
CPC .......... A61F 13/00068 (2013.01); A61F 5/30 (2013.01); A61F 13/00012 (2013.01); A61F 13/00017 (2013.01); A61F 13/00021 (2013.01); A61F 13/00038 (2013.01); A61F 13/00042 (2013.01); A61F 2013/0028 (2013.01); A61F 2013/00102 (2013.01); A61F 2013/00106 (2013.01); A61F 2013/00119 (2013.01)

(58) Field of Classification Search
USPC ......................................................... 602/53
See application file for complete search history.

(56) References Cited

U.S. PATENT DOCUMENTS

| 4,005,709 | A | * | 2/1977 | Laerdal | ............. A61F 13/00021 602/53 |
| 4,205,674 | A | * | 6/1980 | Porat | ................. A61F 13/00021 2/919 |
| 4,991,234 | A | * | 2/1991 | Greenberg | ............. A41D 20/00 2/16 |
| 5,006,401 | A | * | 4/1991 | Frank | ................... A61F 13/0273 128/898 |
| 5,167,613 | A | * | 12/1992 | Karami | ............... A61F 13/0203 602/42 |
| 5,538,500 | A | * | 7/1996 | Peterson | ............... A61F 13/062 602/20 |
| 6,573,419 | B2 | * | 6/2003 | Naimer | ............... A61F 13/0273 602/41 |
| 7,074,982 | B2 | * | 7/2006 | Knutson | ............... A61F 15/008 602/42 |

(Continued)

Primary Examiner — Kim M Lewis

(57) ABSTRACT

A bandage for use at an aggressive bleeding site of a patient is disclosed. The bandage includes a stretchable wrap, an auxiliary strap, a primary absorbent body, and at plural secondary absorbent bodies. The primary absorbent body is located on the inner surface of the wrap. The wrap is arranged to be wrapped about and tightly encircle a portion of the body of a patient at which the bleeding site is located to cause the primary absorbent body to apply pressure thereto. The auxiliary strap is secured to the wrap and is normally held in stowed position on the wrap, but arranged to be moved to an extended position whereupon the secondary absorbent bodies overlies said primary absorbent body and apply pressure thereto and to the underlying aggressive bleeding site.

20 Claims, 1 Drawing Sheet

(56) References Cited

U.S. PATENT DOCUMENTS

2006/0211976 A1\* 9/2006 Ramsey ............. A61B 17/1322
  602/75
2011/0237994 A1\* 9/2011 Russ ................. A61F 13/00034
  602/46

\* cited by examiner

BANDAGE FOR REDUCING BLOOD LEAKAGE FROM AGGRESSIVE BLEEDING SITE

CROSS-REFERENCE TO RELATED APPLICATIONS

This utility application claims the benefit under 35 U.S.C. § 119(e) of Provisional Application Ser. No. 62/072,609, filed on Oct. 30, 2014 entitled Bandage for Reducing Blood Leakage From Aggressive Bleeding Site, whose entire disclosure is incorporated by reference herein and which is assigned to the same assignee as the subject invention.

FIELD OF THE INVENTION

This invention relates generally to medical devices, and more particularly to bandages for absorbing blood leaking from an aggressive bleeding site to facilitate blood clotting.

BACKGROUND OF THE INVENTION

Various types of bandages are commercially available for use in preventing leakage or bleeding from an aggressive bleeding site, such as a dialysis port, or a major wound. However, such bandages have left much to be desired from the standpoint of effectiveness is stopping massive bleeding from such a site. Thus, a need exists for a simple, low-cost, yet effective bandage which will prevent facilitate clotting and minimize blood leakage from an aggressive bleeding site. The subject invention addresses that need.

SUMMARY OF THE INVENTION

In accordance with one aspect of this invention there is provided a bandage for use at an aggressive bleeding site, e.g., a dialysis or some other portal, a substantial wound, etc., of a patient to absorb blood leaking from the site and to facilitate clotting. The bandage comprises a stretchable wrap, an auxiliary strap, a primary absorbent body, and at least one secondary absorbent body. The wrap has an outer surface, an inner surface, a first end, a second end and an intermediate portion. The auxiliary strap has a first end, a second end, an intermediate portion, an outer surface and an inner surface. The at least one secondary absorbent body is fixedly secured on the inner surface of the auxiliary strap at the intermediate portion thereof. The auxiliary strap is secured by the first end thereof to the outer surface of the wrap adjacent the intermediate portion of the wrap. The primary absorbent body is fixedly secured to the inner surface of the wrap at the intermediate portion. The first end of the wrap and the second end of the wrap are arranged to be overlapped to releasably secure the first end of the wrap to the second end of the wrap to cause the wrap to tightly encircle a portion of the body of the patient at which the bleeding site is located to apply pressure thereto, with the primary absorbent body disposed in abutment with and applying pressure to the aggressive bleeding site. The auxiliary strap is arranged to be normally held in stowed position on the wrap, but arranged to be moved to an extended position, whereupon the second end of the auxiliary strap is releasably secured to the outer surface of the wrap such that the at least one secondary absorbent body overlies the primary absorbent body and applies pressure thereto and to the underlying aggressive bleeding site.

In accordance with one preferred aspect of the invention the bandage comprises plural secondary absorbent bodies and the auxiliary strap is folded into an accordion pleated configuration when in its stowed position, whereupon the plural secondary absorbent bodies are disposed close to one another.

In accordance with another preferred aspect of the invention the first end of the wrap comprises one component of a two-component releasably securable fastening system and the outer surface of the wrap comprises the other component of the two-component, e.g., VELCRO®, releasably securable fastening system. The one component at the first end of said wrap is arranged to be releasably secured to the second component on the outer surface of the wrap to cause the wrap to tightly encircle a portion of the body of a patient at which the bleeding site is located to apply pressure thereto.

In accordance with another preferred aspect of the invention the auxiliary strap is stretchable and the second end of the auxiliary strap comprises one component of a two-component, e.g., VELCRO®, releasably securable fastening system, wherein the outer surface of the wrap comprises the other component of the two-component releasably securable fastening system. The one component at the second end of the auxiliary strap may be releasably secured to the second component on the outer surface of the wrap to hold the auxiliary strap in the extended position.

DETAILED DESCRIPTION OF THE PREFERRED EMBODIMENT

Figure 1:
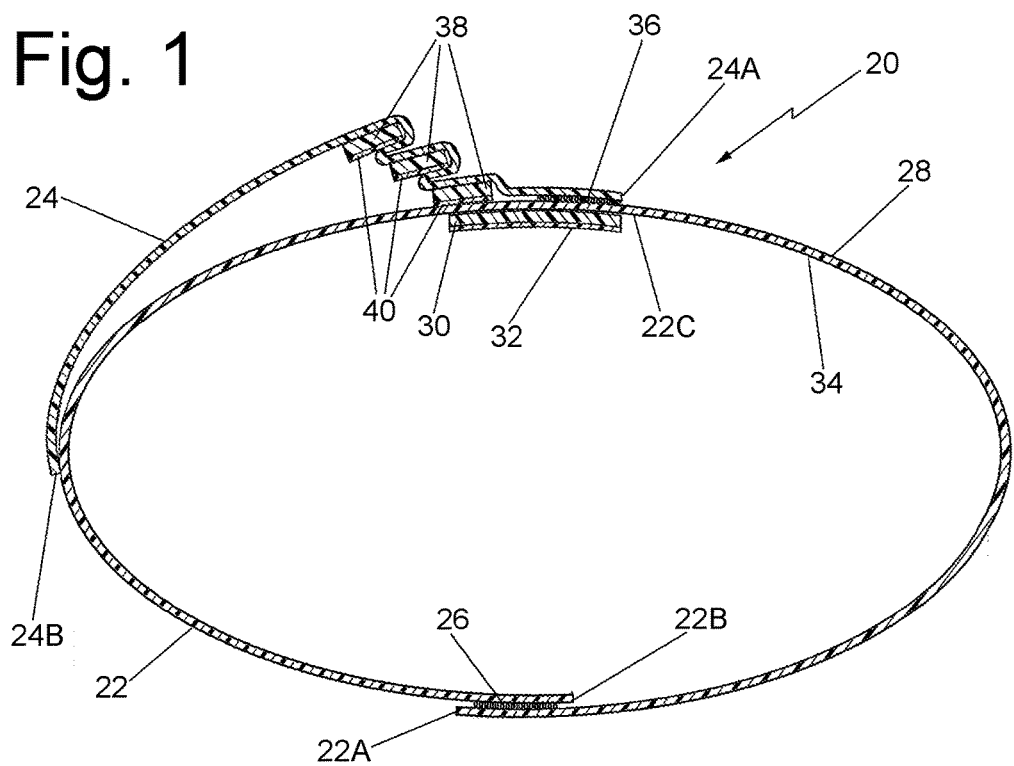
FIG. 1 is vertical sectional view of one exemplary embodiment of a bandage constructed in accordance with this invention and shown in place for preventing blood from an aggressive bleeding site, e.g., a dialysis port, with an auxiliary blood absorbing portion of the bandage held in a stowed or refracted orientation ready for use, if necessary.

Referring now to the various figures of the drawing wherein like reference characters refer to like parts, there is shown at 20 in FIG. 1 one exemplary embodiment of a bandage constructed in accordance with this invention. The bandage 20 basically comprises a stretchable blood-absorbing wrap 22 and an auxiliary blood-absorbing strap 24. The stretchable wrap 22 is in the form of a web of elastic material, e.g., a fabric comprising cotton, polyester and latex-free elastic yarns, which is arranged to be wrapped about a portion of the body of a patient over the aggressive bleeding site, e.g., a dialysis or some other blood port (not shown) or a major wound (not shown). The wrap can be of any suitable length and width appropriate for the anatomy of the patient. In any case, the wrap 22 includes a pair of ends 22A and 22B, and an intermediate portion 22C located between the ends. A releasably securable fastening member 26 is located at the end 22A. The fastening member 26 can be of any construction, but is preferably a patch of a multi-hook component of a two-component releasable fastening system, such as a VELCRO® fastening system. The outer surface 28 of the wrap is preferably in the form of the cooperating component, e.g., a plush or multi-loop component, of the two-component releasable fastening system. Thus, the wrap can be wrapped around to encircle the portion of the patient's body at which the bleeding site is located, e.g., an arm if the bleeding site constitutes a dialysis port, and can be held in place by the releasable engagement of the fastening member 26 onto any portion of the outer surface 28 of the wrap. Since the fastening member can be releasably secured to any portion of the outer surface 28 of the wrap and the wrap is formed of a stretchable material, the user can establish the desired amount of tension in the wrap and hence can establish the amount of pressure that the wrap applies to the encircled anatomy of the patient.

The wrap 22 includes a primary absorbent body 30, which is preferably in the form of a patch or pad of any conventional material to absorb blood and facilitate its clotting. The body 30 preferably includes a non-stick outer surface 32 similar to that used in conventional adhesive strip bandages. The absorbent body 30 is fixedly secured on the inner surface 34 of the wrap at the intermediate portion 22C. A protective liner sheet (not shown) may be releasably secured over the absorbent body 30 to keep it sanitary until the bandage 20 is ready for use. Accordingly, when the wrap 22 is used, i.e., wrapped about the portion of the patient's anatomy where the bleeding site is located, the absorbent body 30 will be brought into tight engagement with that bleeding site and pressure will be applied thereto. Thus, blood which would tend to leak out of the bleeding site will be absorbed by the absorbent body 30 to thereby facilitate clotting.

In some cases, the absorbent body 28 may not be sufficient for very aggressive bleeding sites. Thus, the bandage 20 includes additional means that is operative to staunch or otherwise minimize any excess bleeding. In particular, the bandage 20 makes use of the auxiliary strap 24. That strap basically comprises a web of material, which is preferably the same material as that making up the wrap 22, having a pair of ends 24A and 24B. The end 24B is fixedly secured, e.g., sewn or adhesively secured, to a portion of the outer surface 26 of the web between the intermediate portion 22C and the end 22B. The opposite end 24A of the strap 24 is a free end and includes a patch 36 of a multi-hook component of a two-component releasable fastening system, such as a VELCRO® fastening system, on the inner surface of the strap. The inner surface of the strap 24 also includes at least one, and preferably a plurality of secondary absorbent bodies 38, fixedly secured thereto. Each of the secondary absorbent bodies 38 is of any conventional material to absorb blood and facilitate its clotting, e.g., the same material as that making up the primary absorbent body 28. Moreover, the secondary bodies 38 may be of the same thickness as the primary absorbent body 30, or may be thicker to provide greater absorbency. Each secondary absorbent body 38 preferably includes a non-stick outer surface 40 similar to that on the primary absorbent body 30. A protective liner sheet (not shown) may be releasably secured over the absorbent bodies 38 to keep them sanitary until the auxiliary strap of the bandage 20 is ready for use.

In accordance with one preferred aspect of this invention the auxiliary strap 24 with its secondary absorbent bodies 38 is arranged to be held in a compact, stowed condition, like shown in FIG. 1, until it is needed for use. To that end, the web of material making up the auxiliary strap 24 is arranged to be folded into a corrugated or accordion-like arrangement, with respective ones of each of the secondary absorbent bodies 38 located within respective folds. In order to facilitate the folding of the auxiliary strap 24 each secondary absorbent body 30 is preferably in the form of a somewhat narrow patch or pad. The auxiliary strap 24 is held in place in its stowed condition by the releasable engagement of the multi-hook fastening patch 36 with any desired portion of the cooperating multi-loop component outer surface 28 of the wrap 22.

Figure 2:
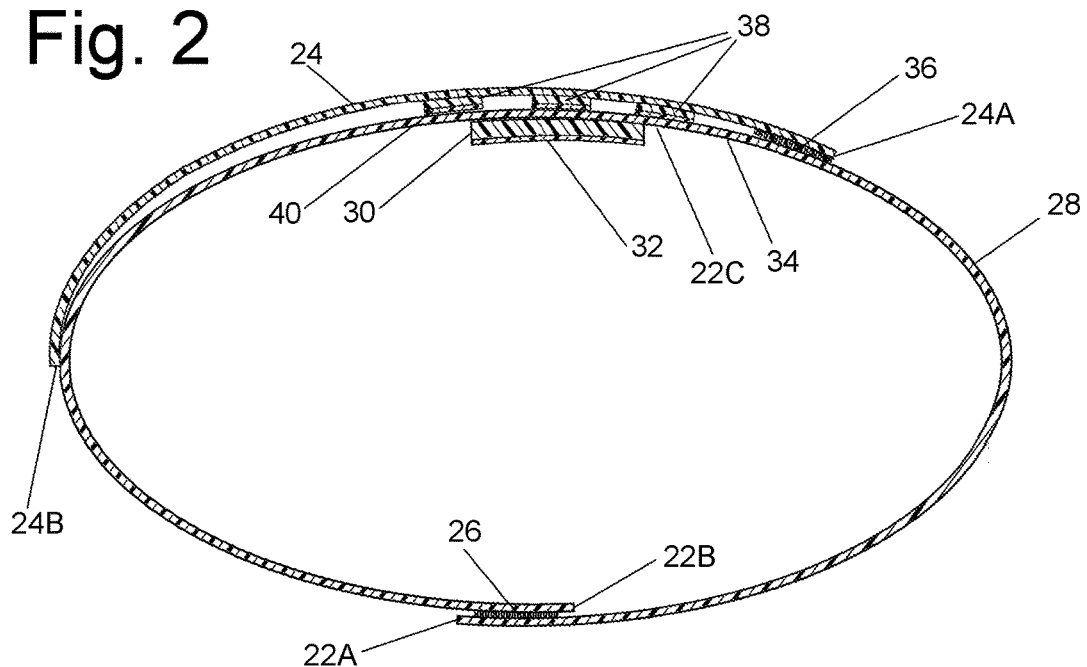
FIG. 2 is a vertical sectional view of the exemplary embodiment of the bandage shown in FIG. 1, but with an auxiliary blood absorbing portion of the bandage extended over the aggressive bleeding site to provide additional absorption.

In the event that the auxiliary strap 24 is needed for use after the wrap has been placed in position with its primary absorbent body 30 in engagement with the bleeding site, all that is necessary is to pull on the end 24A of the strap to release it from engagement with the wrap 22 and then to extend, e.g., stretch, the strap by pulling on it until the multi-hook patch 36 is over a desired portion of the wrap so that the plural secondary absorbent bodies 38 are disposed over the primary absorbent body 28. At this point the multi-hook patch 36 can be brought into engagement with the outer surface of that portion of the wrap 22 to releasably secure the auxiliary strap in that extended, operative position, like shown in FIG. 2, whereupon additional pressure will be applied to the bleeding site by the increased tension provided by the stretched auxiliary strap, and with the secondary absorbent bodies 38 ready to absorb and facilitate clotting of any blood that is not absorbed by the primary absorbent body 30.

It should be pointed out at this juncture that the auxiliary strap 24, need not be the same material as that of the wrap 22. In fact, the strap 24 need not be stretchable. Moreover, the auxiliary strap need not be folded into an accordion like configuration for holding the secondary absorbent bodies 38 in their stowed position. It should also be noted that the subject invention contemplates use of only a single secondary absorbent body and the sizes and shapes of the primary and secondary absorbent bodies, and the size and length of the wrap and the auxiliary strap can be whatever is suitable for a particular bleeding site and application. Moreover, the auxiliary strap 24 may be secured onto the opposite side of the wrap 22 than shown, i.e., the end 24B of the wrap 24 may be fixedly secured to the outer surface 26 of the wrap between the intermediate portion 22C and the end 22A. Further still, while the disclosed preferred embodiment of the invention makes use of VELCRO® type releasably securement fasteners for securing the wrap in place, any other type of releasably securable fastener can be used, e.g., snaps, button, clasps, etc. In fact, it is contemplated that the wrap 22 can be constructed so that the fastening means is not releasably securable, e.g., one or both of the inner surface and outer surfaces at the wrap 22 may include an adhesive thereon to secure the overlapping ends 22A and 22B together. With respect to the auxiliary strap, it too can use other releasably securable fastening means to hold the strap in its stowed condition until ready for use, and for securing its free end 24A to the outer surface of the wrap when the strap is in its extended, operative position.

Without further elaboration the foregoing will so fully illustrate our invention that others may, by applying current or future knowledge, adopt the same for use under various conditions of service.

I claim:

1. A bandage for use at an aggressive bleeding site of a patient to absorb blood leaking therefrom to facilitate clotting, said bandage comprising a stretchable wrap, an auxiliary strap, a primary absorbent body, and at least one secondary absorbent body, said wrap having an outer surface, an inner surface, a first end, a second end and an intermediate portion, said auxiliary strap having a first end, a second end, an intermediate portion, an outer surface and an inner surface, said at least one secondary absorbent body being fixedly secured on said inner surface of said auxiliary strap at said intermediate portion thereof, said auxiliary strap being secured by said first end thereof to said outer surface of said wrap adjacent said intermediate portion of said wrap, said primary absorbent body being fixedly secured to said inner surface of said wrap at said intermediate portion, said first end of said wrap and said second end of said wrap being arranged to be overlapped to releasably secure said first end of said wrap to said second end of said wrap to cause said wrap to tightly encircle a portion of the body of the patient at which the bleeding site is located to apply pressure thereto, with said primary absorbent body disposed in abutment with and applying pressure to the aggressive bleeding site, said auxiliary strap being arranged to be normally held in stowed position on said wrap, but arranged to be moved to an extended position whereupon said second end of said auxiliary strap is releasably secured to the outer surface of said wrap such that said at least one secondary absorbent body overlies said primary absorbent body and applies pressure thereto and to the underlying aggressive bleeding site.

2. The bandage of claim 1 wherein said bandage comprises plural secondary absorbent bodies.

3. The bandage of claim 2 wherein said auxiliary strap is folded into an accordion pleated configuration when in said stowed position, whereupon said plural secondary absorbent bodies are disposed close to one another.

4. The bandage of claim 3 wherein said auxiliary strap is stretchable.

5. The bandage of claim 3 wherein said first end of said wrap comprises one component of a two-component releasably securable fastening system, and wherein said outer surface of said wrap comprises the other component of said two-component releasably securable fastening system, whereupon said one component at said first end of 10 said wrap may be releasably secured to said second component on said outer surface of said wrap to cause said wrap to tightly encircle the portion of the body of the patient at which the bleeding site is located to apply pressure thereto.

6. The bandage of claim 5 wherein said second end of said auxiliary strap comprises one component of a two-component releasably securable fastening system, and wherein said outer surface of said wrap comprises the other component of said two-component releasably securable fastening system, whereupon said one component at said second end of said auxiliary strap may be releasably secured to said second component on said outer surface of said wrap to hold said auxiliary strap in said extended position.

7. The bandage of claim 6 wherein said stretchable material comprises an elastic fabric.

8. The bandage of claim 7 wherein said fabric comprises cotton, polyester and latex-free elastic yarns.

9. The bandage of claim 6 wherein said primary absorbent body includes a non-stick outer surface.

10. The bandage of claim 6 wherein said at least one secondary absorbent body includes a non-stick outer surface.

11. The bandage of claim 10 wherein said at least one secondary absorbent body includes a non-stick outer surface.

12. The bandage of claim 1 wherein said auxiliary strap is stretchable.

13. The bandage of claim 12 wherein said second end of said auxiliary strap comprises one component of a two-component releasably securable fastening system, and wherein said outer surface of said wrap comprises the other component of said two-component releasably securable fastening system, whereupon said one component at said second end of said auxiliary strap may be releasably secured to said second component on said outer surface of said wrap to hold said auxiliary strap in said extended position.

14. The bandage of claim 1 wherein said first end of said wrap comprises one component of a two-component releasably securable fastening system, and wherein said outer surface of said wrap comprises the other component of said two-component releasably securable fastening system, whereupon said one component at said first end of said wrap may be releasably secured to said second component on said outer surface of said wrap to cause said wrap to tightly encircle the portion of the body of the patient at which the bleeding site is located to apply pressure thereto.

15. The bandage of claim 1 wherein said second end of said auxiliary strap comprises one component of a two-component releasably securable fastening system, and wherein said outer surface of said wrap comprises the other component of said two-component releasably securable fastening system, whereupon said one component at said second end of said auxiliary strap may be releasably secured to said second component on said outer surface of said wrap to hold said auxiliary strap in said extended position.

16. The bandage of claim 1 wherein said stretchable material comprises an elastic fabric.

17. The bandage of claim 16 wherein said fabric comprises cotton, polyester and latex-free elastic yarns.

18. The bandage of claim 1 wherein said primary absorbent body includes a non-stick outer surface.

19. The bandage of claim 18 wherein said at least one secondary absorbent body includes a non-stick outer surface.

20. The bandage of claim 1 wherein said at least one secondary absorbent body includes a non-stick outer surface.

* * * * *